United States Patent [19]

Meisch

[11] 4,417,892
[45] Nov. 29, 1983

[54] URINE DRAINAGE BAG OUTLET TUBE AND METHOD FOR ELIMINATING OR REDUCING MIGRATION OF BACTERIA

[75] Inventor: Charles E. Meisch, Hasbrouck Heights, N.J.

[73] Assignee: C. R. Bard, Inc., Murray Hill, N.J.

[21] Appl. No.: 336,289

[22] Filed: Dec. 31, 1981

[51] Int. Cl.³ .............................................. A61M 1/00
[52] U.S. Cl. .................................. 604/323; 604/326; 604/349; 422/28
[58] Field of Search ..................... 604/317, 323–326, 604/349, 350; 128/760, 764, 766, 767, 771; 422/36, 37, 28, 236

[56] References Cited

U.S. PATENT DOCUMENTS

| | | | |
|---|---|---|---|
| 1,325,291 | 12/1919 | Hood | 422/236 |
| 3,924,747 | 12/1975 | Gerner | 206/484 |
| 4,004,590 | 1/1977 | Muriot | 604/326 |
| 4,342,395 | 8/1982 | Brown | 206/530 |
| 4,372,313 | 2/1983 | Villari et al. | 128/767 |

*Primary Examiner*—C. Fred Rosenbaum
*Assistant Examiner*—J. L. Kruter
*Attorney, Agent, or Firm*—Dennison, Meserole, Pollack & Scheiner

[57] ABSTRACT

A urine drainage bag having an outlet tube provided with a hydrophilic coating on its inner wall surface and an antimicrobial substance such as iodine carried within a frangible capsule adapted to be received within the tube and said substance being absorbable by the coating when the capsule is ruptured. A method of treating a urine drainage bag outlet tube to prevent multiplication or growth of microorganisms utilizing a frangible carrier within the tube is taught.

10 Claims, 3 Drawing Figures

URINE DRAINAGE BAG OUTLET TUBE AND METHOD FOR ELIMINATING OR REDUCING MIGRATION OF BACTERIA

BACKGROUND OF THE INVENTION

The present invention relates generally to closed system urinary drainage bags of the type conventionally used in hospital environments where it is frequently necessary to collect urine from patients. Such urine drainage bags are routinely used by post-operative patients as well as those with urological disorders. In use, the patient is catheterized and the catheter then connected to the drainage bag through a length of plastic tubing. The bag is normally supported below the level of the patient either from a bed rail or other support and the urine drains by gravity from the patient through the catheter, the tubing and then into a bag via a drip chamber. The bag may be emptied from time to time by means of an outlet tube which is normally closed to prevent leakage. The tube may discharge its contents into any convenient receptacle and then the outlet tube is clamped and the bag reused for the same patient. More specifically, the invention herein resides in a specific construction of the outlet tube for such a urine bag to prevent or eliminate build up and migration of bacteria through the outlet tube into the bag. The invention also contemplates a novel method for elimination or reduction of such bacteria in the outlet section or tube.

The catheterized urinary track is one of the most common sites of hospital-acquired infection and in fact accounts for almost thirty percent of such infections. Significant improvements in the prevention of catheter associated infection has been by use of what are known as closed sterile drainage systems. Despite these advances, still over twenty percent of patients with indwelling catheters continue to acquire urinary infections. See Garibaldi et al, New England J. Med., 291:215–219, 1974. Urine collection bags must be emptied at frequent intervals usually at least once every shift and the removal of bacterially contaminated urine can lead to the spread of urine infection. It is even possible for a patient in the same ward or room shared with a catheterized patient to acquire the infection. In order to minimize cross-contamination, the collected urine must be maintained in sterile condition during the collection period, even when the urine has a high bacterial count when it enters the drainage bag.

Despite the use of the most careful aseptic techniques almost fifty percent of catheterized patients develop an infection when the catheter is in place for twenty-four hours and approximately ninety-eight percent or even more develop an infection of after four days of use of such catheters. This of course is quite harmful to the patient and subjects them to the risk of cystitis and life threatening septicemia. Arch. Internal Med., Vol. 110:703–711 (1962) and Lancet, Vol. 1, 310–312 (1960). The above-noted infections occur due to many circumstances. These include prolonged use of indwelling Foley-type catheters which are often accompanied by absence of sterile insertion and maintenance techniques; having the catheter connected to clean but not sterilized drainage collection containers; and others. The presence of urinary pathogens in the container which multiply and enter the urinary track through the ascending catheter which is a major pathway of infection is quite important. Various attempts have been made to reduce the migration of bacteria through the closed system including the bag, the drip chamber and the tubing connected to the catheter.

The patent to Jinkens et al, No. 3,332,442 employs a connector between a catheter and a urine drainage bag for preventing movement of bacteria from the bag to the patient. The three patents of Langston et al, Nos. 4,236,517; 4,193,403; and 4,241,733 show a dispensing device which releases paraformaldehyde to control the multiplication of pathogens and prevent migration in catheters. Shaffer U.S. Pat. No. 4,233,263, teaches adding of hydrogen peroxide solution periodically to a urine bag for prevention of bacterial growth.

Other attempts have been made to provide a one way inlet valve into the urine bag to prevent upward migration. Note Overment U.S. Pat. No. 3,312,221 and Leibinsohn 4,232,677.

Other attempts have been made to treat the catheter itself with an antibacterial substance. Note U.S. Pat. No. 3,598,127 and the Shepard et al patent Nos. 3,566,874 and 3,695,921 which relate to an antibiotic material in a hydrophilic catheter coating.

SUMMARY AND OBJECTS OF THE INVENTION

In normal use of the conventional urinary drainage bag, transmission of infection via the outlet drainage tube is of major concern. In this invention an antimicrobial dispensing system which may allow a timed released action to a specific area of the outlet drainage tube is a method of reducing infections at this site. The invention includes an encapsulated glass ampule which may be filled with an appropriate antimicrobial substance. The ampule may be covered with a fabric mesh or someother porous membrane which is then inserted into the outlet drainage tube which itself has been treated with a hydrophilic coating to absorb the antimicrobial substance. Upon breaking of the ampule by pinching the outlet tube the antimicrobial substance will be absorbed into the fabric of the ampule and ultimately into the hydrophilic coating of the outlet tube.

The purpose of this invention is to prevent organisms from entering urinary drainage bag systems via an opening to the outside atmosphere. It is a primary object of the present invention to provide a specially coated outlet tube for a drainage bag and a carrier for an antimicrobial substance which may be activated prior to use of the device to prevent or at least reduce bacterial migration from the atmosphere into the outlet tube.

It is a further object of the invention to provide a new method for preventing organisms from entering urinary drainage bags via the outlet tube. A further object of the invention is to provide a new urine drainage bag and outlet tube system and a special dispensing device in the outlet tube for preventing the multiplication and control of the migration of pathogens from the atmosphere into the bag through the drainage tube. Another object of the invention is to provide a specific carrier in the form of a frangible ampule containing antimicrobial substances that may be transfered to a hydrophilic coating on the interior walls of a drainage bag outlet tube.

Various other objects and advantages of my invention will be readily apparent from the following detailed description taken in conjunction with the drawings in which an exemplary embodiment of the invention is shown.

DESCRIPTION OF PREFERRED EMBODIMENT

Figure 1:
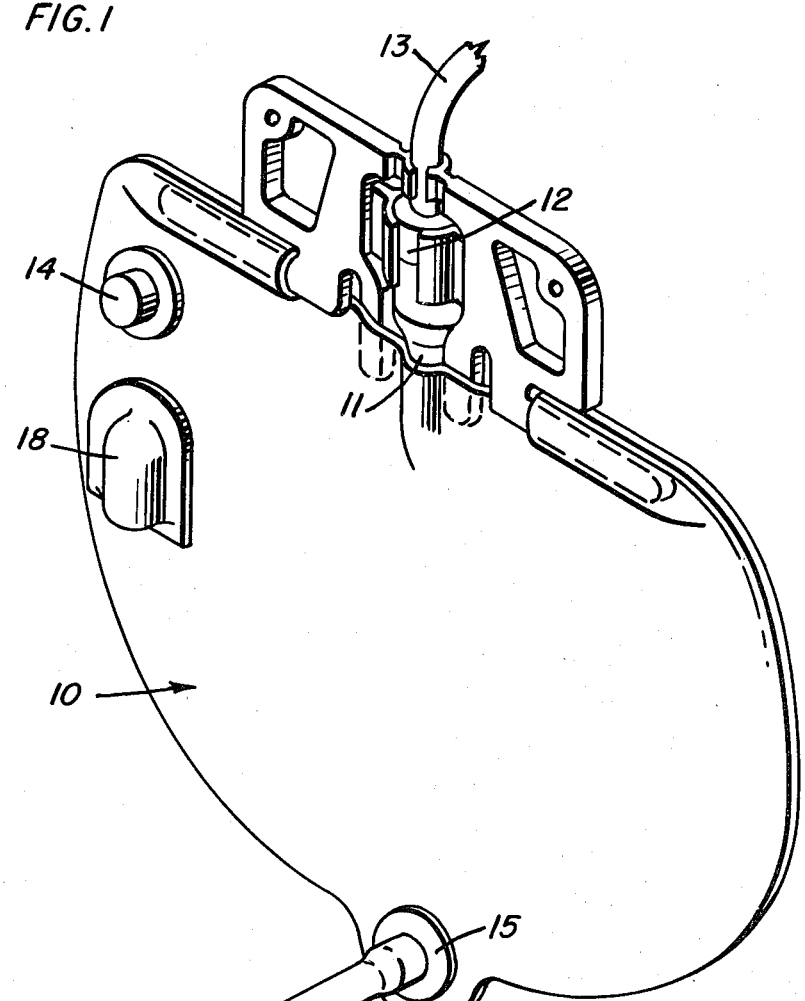
FIG. 1 is a perspective view of a conventional urine drainage bag and showing the outlet tube in broken apart fashion.
Figure 2:
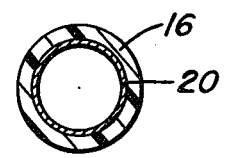
FIG. 2 is an enlarged cross section of the outlet tube taken along the lines 2—2 of FIG. 1.
Figure 3:
FIG. 3 is an elevation of a typical covered glass ampule used in the outlet tube.

Referring now to the drawings, a conventional closed system urine drainage bag is shown generally at 10 and is formed by peripherally heat sealing or otherwise securing a pair of flat vinyl or PVC sheets. The bag is provided with an inlet 11 adjacent the top thereof for reception of a conventional drip chamber 12 and its associated tubing 13 which connects to a catheter which in turn is inserted in the urethral canal of the patient. An air vent and bacterial filter 14 is conventionally provided on one face of the bag.

The bag also includes a drain 15 terminating in an outlet tube or conduit 16 which may be formed of latex or any other suitable material, and which may be clamped off when not in use in a well known manner by means of the spring pinch clamp or valve 17 which is received about the outlet tube. The free end of the outlet is received in a protective housing 18 heat sealed to one face of the urine drainage bag.

The interior surface of outlet tube 16 is coated with a hydrophilic material 20 that is capable of absorbing and also of receiving bactericidal substances. Various hydrophilic coatings may be used and the art teaches means for binding hydrophilic polymers to rubber. Note for example Shepherd U.S. Pat. No. 3,695,921.

A preferred coating of hydrophilic acrylate and methacrylate polymer may be used. This is normally applied by dipping the catheter in a casting syrup of the monomer or partially polymerized monomer and then completing the polymerization.

The hydrophilic monomer used may be a hydroxy lower alkyl acrylate or methacrylate, hydroxy lower alkoxy lower alkyl acrylate or methacrylate, as for example 2-hydroxyethyl acrylate, 2-hydroxyethyl methacrylate, diethylene glycol monomethacrylate, diethylene glycol monoacrylate, 2-hydroxy propyl acrylate, 2-hydroxy propyl methacrylate, 3-hydroxy propyl acrylate, 3-hydroxy propyl methacrylate, or dipropylene glycol monomethacrylate. Other compositions might also be employed for this purpose as desired.

The specific antimicrobial substance or bactericidal material is left to the choice of the manufacturer however such substance must readily adhere to the hydrophilic coating which in turn will absorb the substance. It has been found that a strong iodine solution or Lugols solution will work in this manner. Among other agents that could be used are mercurial compounds, sulfur compounds, broad spectrum antiobiotics, hydrogen peroxide, halogen complexes, betadyne, and many other substances known to have antiobiotic or biocidal properties.

The bactericidal substance is conveniently carried prior to use in a frangible ampule shown at 25 which includes a glass capsule 26 which is enclosed within a fabric mesh cover 27 having opposed end portions 28.

In use, the ampule is inserted within the free end of the outlet tube 16 as shown in FIG. 1. The ampule may be retained in the outlet tube until the bag is ready for use. At this time, the ampule is crushed to release the bacteristatic or antimicrobial substance which will then adhere to the hydrophilic coating of the outlet tube. The coating will absorb the material and release the substance to maintain a sterile pathway and thus eliminate chances of organisms entering the system when the system is open for drainage or irrigation purposes. The end 28 of the ampule may be manually grasped and the ampule removed or alternatively the capsule may be discarded when the first emptying of the drainage bag occurs. Removal of the ampule of course will include all fragments of the glass along with any excess antimicrobial substance.

It will be noted that the ampule may be inserted during normal manufacturing conditions and there will be no loss of the antimicrobial properties since the substance is totally sealed within the glass capsule 26. The capsule may be broken by merely pinching the outlet tube adjacent to the ampule which will cause release of the contents thereof in a known manner.

Activation in the manner described above results in complete protection of the outlet tube agaist migration of bacteria and other organisms from the outside of the closed system.

I claim:

1. An outlet for a urine drainage bag, comprising an elongated outlet tube secured to the bottom portion of the drainage bag, at least a portion of the interior of said tube having a hydrophilic coating means thereon, a normally totally sealed frangible ampule containing an antimicrobial substance received in said outlet tube, the antimicrobial substance being absorbed by said coating means on the tube interior when the frangible ampule seal is broken.

2. An outlet as defined in claim 1, wherein the frangible ampule has a fabric mesh or someother porous membrane covering.

3. The outlet as defined in claim 2 wherein the frangible ampule is made of glass.

4. The outlet as defined in claim 1 wherein the antimicrobial substance is iodine.

5. The outlet as defined in claim 1 wherein the hydrophilic coating is a polymer.

6. The outlet as defined in claim 5 wherein the coating is an acrylate or methacrylate polymer.

7. A method of treating the outlet tube of a urinary drainage bag to prevent passage, multiplication or growth of microorganisms comprising the steps of coating at least a portion of the interior of said tube with a hydrophilic material means, inserting a totally sealed frangible ampule carrier containing an antimicrobial substance into said tube where it may remain until ready for use, and breaking said carrier, whereby the antimicrobial substance may be absorbed by the hydrophilic coating means on said tube.

8. A method as set forth in claim 7, wherein the hydrophilic coating means is a polymer.

9. A method as set forth in claim 8 wherein the coating means is an acrylate or methacrylate polymer.

10. A method as set forth in claim 7 wherein the antimicrobial substance is iodine.

* * * * *

UNITED STATES PATENT AND TRADEMARK OFFICE
CERTIFICATE OF CORRECTION

PATENT NO. : 4,417,892
DATED : November 29, 1983
INVENTOR(S) : Charles E. Meisch It is certified that error appears in the above—identified patent and that said Letters Patent are hereby corrected as shown below:

The Inventor should read as follows:

"Inventor: Charles E. Meisch, Hasbrouck Heights, NJ; and
Douglas G. Smillie, Chatham Township, NJ. "

Signed and Sealed this

Tenth Day of April 1984

[SEAL]

Attest:

GERALD J. MOSSINGHOFF

Attesting Officer    Commissioner of Patents and Trademarks